United States Patent [19]

Kass

[11] Patent Number: 5,106,744
[45] Date of Patent: Apr. 21, 1992

[54] METHOD OF STAINING MONOCYTES AND COMPOSITIONS THEREOF

[75] Inventor: Lawrence Kass, Hinckley, Ohio
[73] Assignee: Cytocolor Inc., Hinckley, Ohio
[21] Appl. No.: 606,330
[22] Filed: Nov. 1, 1990
[51] Int. Cl.$^5$ .............................................. G01N 1/30
[52] U.S. Cl. ..................... 435/240.2; 424/3; 436/63; 436/174; 436/805; 435/29; 435/34
[58] Field of Search .............. 424/3, 7.1; 436/63, 436/64, 164, 166, 174, 805; 435/1, 29, 34, 39, 240.2

[56] References Cited

U.S. PATENT DOCUMENTS

| | | | |
|---|---|---|---|
| 3,906,120 | 9/1975 | Geating | 424/3 X |
| 4,020,006 | 4/1977 | Parker | 436/10 |
| 4,070,495 | 1/1978 | Berger et al. | 424/3 |
| 4,581,223 | 4/1986 | Kass | 424/3 |
| 4,714,606 | 12/1987 | Kass | 435/34 X |
| 4,810,487 | 3/1989 | Kass | 424/3 |
| 4,996,040 | 2/1991 | Kass | 534/761 X |

Primary Examiner—David L. Lacey
Assistant Examiner—Jeffrey R. Snay

[57] ABSTRACT

This invention is directed to the cytology of blood, bone marrow and lymph node cells and to the method of differentiating, identifying and enumerating monocytes among a plurality of cells of hematopoietic origin. More specifically, the invention is directed to stained cells and to the use of a cationic sulfur-containing azo dye capable of staining monocytes a bright red-violet color. The dye is a water soluble quaternary azo dye identified in the Colour Index as Basic Blue 54 (C.I. 11052). The stained monocytes obtained by the process of this invention have color characteristics which permit the identification and differentiation of said cells by use of various instruments including, for example, an image analyzer, microscope, photo microscope, and the like.

26 Claims, 1 Drawing Sheet

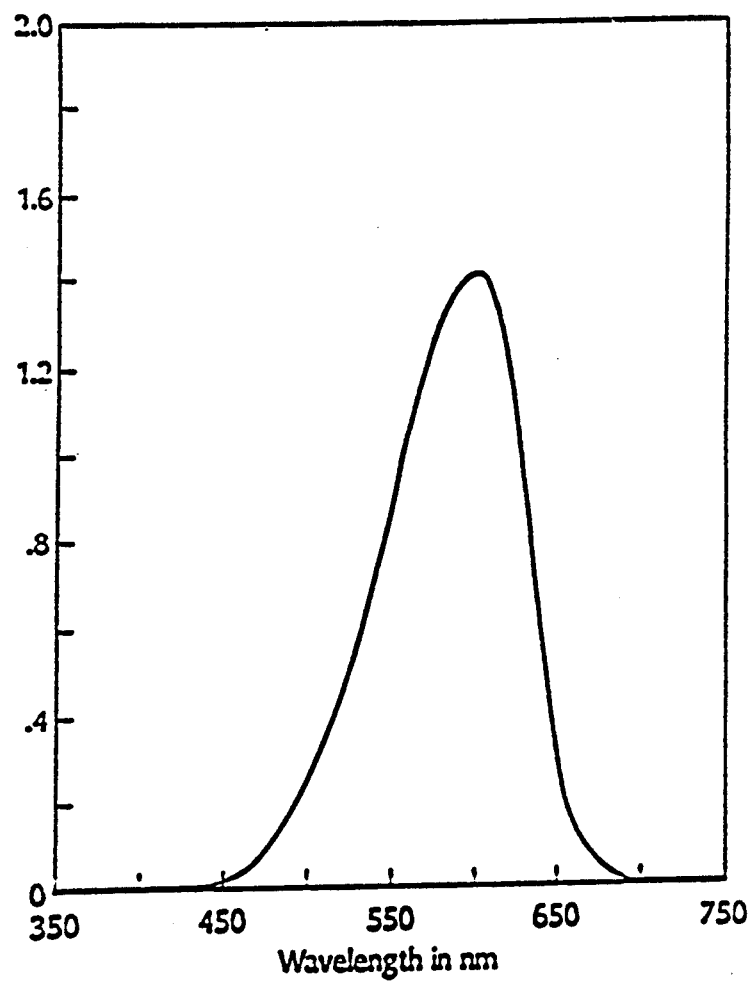
FIG._1

METHOD OF STAINING MONOCYTES AND COMPOSITIONS THEREOF

BACKGROUND OF THE INVENTION

This invention relates to the use of a substantially pure, water soluble azo dye i.e. Basic Blue 54 for the cytological preparation of a fixed biopsy specimen derived from human blood, bone marrow, lymph nodes and other specimen of hematopoietic origin. The use of a water soluble azo dye (identified in the Colour Index as Basic Blue 54 in accordance with this invention, is an advance over the prior art (Romanowsky and Malachowski) wherein a mixture of dyes were used for staining biopsy specimens. The stained cells of hematopoietic origin have excellent Colours stability and are remarkably clear with respect to cellular detail and brilliance of cell structure.

Blood contains a variety of cells. The most numerous cells are the erythrocytes, or red blood cells, which carry out the exchange of oxygen and carbon dioxide between the lungs and the body tissues. The minor population of cells are the leucocytes, or white blood cells, which control the immuno response system of the body and defend the body against infecting organisms and foreign agents both in the tissues and the bloodstream. The leucocyte population in blood is further defined by a number of subclasses which play distinct roles in the immune response. For example, the relative number cells in various subclasses of lymphocytes (about 20% of the leucocyte population) is likely to change in various disease states. Identification of cells of the various subclasses provides an indication of the relative well being of the patient.

The staining of biological cells and tissues with dyes, in order to differentiate one from another or to render them more easily observable under a microscope or other means is known in the art. By such means it is possible to differentiate, for example, among the five types of peripheral blood leucocytes: the neutrophils, eosinophils, basophils, lymphocytes, and monocytes; the difference between cancerous and normal cells; and the difference between mature and immature cells. This differentiation enables the cytologist to diagnose certain diseases.

More specifically, Ehrlich introduced the use of dyes to effect or enhance cell differentiation in human biopsy specimens particularly blood cells. Ehrilich's dyes were superceded, however, by the use of mixtures of dyes identified as Romanowsky dyes which have been modified to include mixtures such as methylene blue, modified methylene blues, eosins, azures and methylene violet. These mixtures of dyes have been generally classified as panoptic stains because of the wide range and broad spectra of hues and chroma produced when reacted with a fixed biological specimen such as human blood. As early as 1891, Romanowsky and Malachowski developed mixtures of polychromed methylene blue, azure and methylene violet. Other contributors include Unna (1891), Nocht (1898), Jenner (1899), Leishman (1901), Wright (1902), May-Grunwald and Giemsa (1902), MacNeal (1906) and Lillie (1943).

The diagnosis of hematological disorders has been achieved, for the most part, by enumeration and identification of formed elements of the peripheral blood and bone marrow. The basis of hematological diagnosis includes the use of light microscopic examination of a panoptically stained specimen of blood cells, lymph node cells, or bone marrow cells. This type of examination provides information sufficient to make a diagnosis which parallels the developments of panoptic light microscopy. Cytochemical stains have been developed to identify cell types more precisely than was possible by using panoptic stains. Cytochemistry represents biochemistry on a microscopic and submicroscopic level. When applied to cells and tissue, cytochemical stains identify enzymes, substrates and organelles. As biochemical probes, cytochemical stains often provide valuable insights regarding aberrations of cellular metabolism. Moreover, cytochemical stains can be selective for one cell type compared to another and therefore such stains have been used in various diagnostic processes especially in making distinctions between various cytological types of acute leukemias and preleukemic disorders.

With the development of the synthetic organic dyes, various investigators experimented with supravital stains by adding these dyes to freshly obtained samples of blood or suspension of cells. It was rapidly ascertained that some of the cells were stained with one or more of the dyes whereas other cells were not. Subsequent to the development of supravital staining of blood cells, Ehrlich found the need for a more stable, permanent preparation of blood cells that could be examined under the microscope. Recognizing the difficulties in cell identification in viewing suspensions of unstained cells, Ehrlich devised a stain composed of orange G, acid fuschin and methyl green. On the basis of differential coloration of leukocytes with a mixture of dyes, Ehrlich identified and named most of the blood leukocytes known today. Ehrlich's contribution was remarkable in that by using a plurality of dyes he was able to detect the difference in colors that were distinctive for various cell types. For example, those cells whose granules showed affinity for eosin were called eosinophils. Recognizing that some cells stained differently than the color of the dye in solution, the term metachromasia was popularized and applied to the granules of mast cells. At present, staining techniques form the basis of modern morphological hematology and the nomenclature of various cell types.

However, early in the history of the morphologic and cytochemical diagnosis of blood disorders, it was found that examination of only panoptically stained specimens of blood or bone marrow was not sufficient to make a diagnosis. While some investigators were popularizing the supravital stains, others were describing cytochemical stains for blood cells that could be used on dried, fixed preparations of blood or bone marrow. It became apparent that there were some blood cells that had peroxidase activity while other cells did not. The peroxidase test was the first stain that reliably distinguished between granulocytic cells which contain activity of peroxidase and lymphoid cells which did not contain peroxidase activity. The peroxidase stains with chromophoric modifications and increased use in immunology remain one of the most useful stains in the cytochemistry of blood cells and is the basis for one of the current automated leukocyte differential counting instruments.

As a staining technique, however, cytochemistry has limitations with respect to age of sample, type of fixative, pH, presence or absence of heavy metal cations, deterioration of the substrate, time and temperature of the staining reaction, etc. These are all variables that affect the cytochemical stain. In addition, any impurities in the organic dyestuff as well as variability in the composition of the dye stuff causes alterations in the staining reaction. However, by using cytochemical stains, it is possible to identify the presence or absence of substances in one cell type contrasted to another or any increase or decrease in the quantity of such substance in those cell types. Quantitatively, these differences assume a diagnostic importance when they reflect differences in one cell type compared to another, and in normal cells compared to abnormal or pathological blood cells.

In several instances, specific diseases have cytochemical profiles that complement the traditional microscopic examination of panoptically stained preparations. There are a variety of hematologic disorders wherein cytochemical tests have diagnostic value. Complementing the conventional light microscopy of panoptically stained specimens of blood or bone marrow, cytochemical stains have improved the precision of hematological diagnosis with the recognition that these stains can reveal properties that are distinctive for one cell type compared to another. Cytochemical stains have found increased application in the study of blood, lymph node and bone marrow specimens. For the most part, these stains detect increased or decreased amounts of an enzyme or a metabolite that reflect the pathophysiological condition of a disordered cell. While the exact mechanism or chemistry responsible for the production of the cytochemical abnormalities are unknown, many of these abnormalities are sufficiently distinctive to make them useful diagnostically. As a diagnostic tool for cellular hematology, cytochemistry represents a rapid and inexpensive method to distinguish one cell type from another on the basis of characteristic properties. With advances in dye chemistry one can anticipate further improvements in the cytochemistry of blood cells and the precision of hematological diagnosis in the future. Discussions of cytochemical stains can be found in Cytochemical Stains for Blood and Bone Marrow Cells and Cystobiology of Leukemias and Lymphomias, by L. Kass, M.D., Raven Press, New York, New York, Pages 161-177, 1983, and Lawrence Kass, M.D. Leukemia Cytology and Cytochemistry, published by J.B. Lippincott, Philadelphia, 1982.

In 1898, Ehrlich and Lazarus described a large transitional cell in the peripheral blood. This cell had abundant cytoplasm, and convoluted nucleus. Most likely, this cell was a monocyte. In 1912, Schilling named a similar appearing cell "monozyten". In 1913, Reschad and Schilling described the first case of monocytic leukemia. In panoptically stained preparations of peripheral blood or bone marrow, monocytes are large mononuclear cells with indented or convoluted nuclei, coarse appearing nuclear chromatin strands, and abundant cytoplasm that sometimes contains a few azurophilic granules. In living monocytes, pseudopodia can be seen at the cytoplasmic borders, and the cell displays random movement on a glass coverslip.

For more precise identification of the monocyte, the cytochemical reaction for nonspecific esterase activity has been used. With either alpha naphthyl acetate or preferably alpha naphthyl butyrate as the substrate and fast blue BBN or hexazotized pararosanalin as the coupler, activity of nonspecific esterase is intense in monocytes and in macrophages which is the end stage cell of the monocytic series. Furthermore, nonspecific esterase activity in monocytes is sensitive to inhibition by sodium fluoride, and can be obliterated if sodium fluoride is added to the incubation mixture. Monoclonal antibodies may be used also to identify monocytes, but these antibodies may show cross-reactivity with other cells thereby reducing the specificity for monocytes.

In bone marrow, the promyelocyte is the precursor cell of the monocyte. The monocyte is known as the scavenger cell of the blood. It actively phagocytizes or engulfs foreign particles, such as bacteria, and destroys them. Increased numbers of monocytes are found in the blood in a variety of disorders, such as acute and chronic infections, tropical disorders such as schistosomiasis, syphilis, trypanosomiasis, tuberculosis, myelodysplastic disorders (preleukemic conditions), and monocytic leukemia. Recently, it has been shown that the HIV virus responsible for AIDS can reside unharmed within the cytoplasm of monocytes, and thereby be disseminated throughout the body by these cells. Increasingly, the monocyte has become important in understanding the immune process, even though its role in immunity is complex and critical.

SUMMARY OF THE INVENTION

This invention is directed to the cytology of blood, bone marrow and lymph node cells and to the method of differentiating, identifying and enumerating monocytes among a plurality of cells of hematopoietic origin. Specifically, the invention is directed to stained cells and to the use of a cationic sulfur-containing azo dye capable of staining monocytes a bright red-violet color. The dye is a water-soluble quaternary azo dye identified in the Colour Index as Basic Blue 54 (C.I. 11052). The stained monocytes have color characteristics which permit the identification and differentiation of said cells by use of various instruments.

Accordingly, it is an object of this invention to provide a single, substantially pure, water soluble azo dye for use in staining fixed cells of hematopoietic origin.

It is another object of this invention to provide cells of hematopoietic origin initially treated in a fixative and stained with a water soluble azo dye (Basic Blue 54) and washed in an acid buffer to obtain stained cells having individual color characteristics which permit the differentiation, identification and enumeration of monocytes.

It is a further object of this invention to provide a method of staining a plurality of fixed cells of hematopoietic origin with an azo dye to obtain stained cells having individual color characteristics which permit the differentiation, identification and enumeration of monocytes by means of an instrument.

These and other objects will be apparent from a further and more detailed description of the invention as follows.

FIG. 1 shows the absorbance curve of an aqueous solution of Basic Blue 54 (Basacryl blue GL). There is a single peak with an extinction coefficient of 600nm.

DETAILED DESCRIPTION OF THE INVENTION

This invention is directed to a composition and the method of differentiating, identifying and enumerating monocytes among a plurality of cells of hematopoietic origin selected from the group consisting of blood cells, bone marrow cells, and lymph node cells. The method comprises fixing said cells in a fixative, e.g. a solution of alcohol and staining said fixed cells with staining amounts of a water soluble azo dye, identified in the Colour Index as Basic Blue 54, to obtain a plurality of stained cells. The blood cells, lymph node cells and bone marrow cells may comprise both normal and abnormal cells, e.g. the plurality of cells may comprise malignant cells. The stained cells have color characteristics which permit the differentiation, identification and enumeration of the monocytes. The stained cells may be differentiated by use of various instruments including an image analyzer, microscopes, photomicroscopes, an absorbance light source or any other type of diagnostic instrument.

The cells of hematopoietic origin including blood cells can be fixed in a variety of fluids known as fixatives. Fixatives are generally classified into two classes based on their ability to coagulate proteins. The coagulant fixative include, for example, the absolute alcohols such as methanol or ethanol, formaldehyde, trichloroacetic acid, picrics, etc. The ideal fixative should not shrink nor swell the tissue under examination or change the size thereof. However, most fixatives result in some shrinkage or swelling of the tissue. The degree of alteration depends on the nature of the tissue and the fixative employed. In general, anhydrous fixatives such as acetone or absolute alcohols cause shrinkage. A typical example of fixing lymph node tissue is accomplished by using a solution of formalin or absolute alcohols such as methanol. A solution of formalin is an excellent general purpose fixative in that it has the ability to add to the side groups of certain amino acids and thereby denatures the protein and renders it insoluble. Absolute alcohol such as methanol or other anhydrous fixatives are capable of denaturing protein by coagulation and rapid dehydration. Fixatives useful for purposes of this invention, e.g. testing of blood and the like are well known and may be found in the text, incorporated herein by reference, by S.W. Thompson and R.D. Hunt entitled Selected Histochemical and Histopathological Methods, published by Charles C. Thomas, Springfield, Ill.

Generally, the cells of hematopoietic origin are initially treated or exposed to a fixative, e.g., an alcohol such as methanol, etc., at ambient temperatures. After washing off the fixative, e.g. with water and/or alcohol etc., the fixed cells are stained with staining amounts of an aqueous solution of the quaternary azo dye. Preferably, the cells are stained with an aqueous alkaline solution of the azo dye. Effective amounts of the Basic Blue 54 needed to stain the fixed cells range up to about 2% or more and preferably about 1% by weight. The water soluble quaternary azo dye may be in solution, in water alone or in water containing the azo dye and at least one buffering agent to adjust the pH. The cells i.e. blood cells can be fixed and then stained or the azo dye can be added to the fixative or any variation thereof, provided the stained cells are treated with an acid buffer below about pH 6.0.

More specifically, the process of this invention includes the following variations:

First, a methanolic solution of Basic Blue 54 azo dye is added to the fixed cells for about 3 minutes. Then an aqueous alkaline buffer is added to the methanolic solution of the dye. After 3 minutes, the slides are washed in aqueous acid buffer (e.g. acetic acid/sodium acetate), dried and mounted. Second, a methanolic solution of Basic Blue 54 is applied to cells for about 3 minutes. Then an aqueous alkaline buffered solution of Basic Blue 54 azo dye is added directly to the methanolic solution. After about 3 minutes, the cells are washed in an acidic buffer, dried and mounted. Third, the cells are fixed in absolute methanol for about 3 minutes and the methanol is washed off with distilled water. Then the cells are stained with an aqueous alkaline buffered solution of Basic Blue 54 azo dye for about 3 minutes and then washed in an aqueous acid buffer, dried and mounted.

It is common practice to add the buffering agents to adjust the hydrogen and hydroxyl ion concentration of the particular aqueous system. Buffering agents should be used in the lowest possible concentration to adjust the ion concentration of the particular medium. The buffering capacity of a buffering system is referred to as its beta value and is defined as the amount of acid or alkali needed to change the pH by 0.1 unit. Buffering agents are recognized as belonging to several categories including a variety of acids, bases and salts. Various mixtures are useful to stabilize the pH values of a particular system or fixative in a biochemical reaction. The desired pH of a particular aqueous system can be obtained by mixing different reagents including various acids, bases or salts such as acetic acid, ammonia acetate, the alkali metal salts such as lithium hydroxide, sodium hydroxide, potassium hydroxide, the alkali metal phosphates, alkali metal acetates, carbonates, bicarbonates and the like. Buffering systems can be obtained by using any of the acids or acid salts including the low molecular weight weak organic acids alone or in combination with the alkali metal salts such as citric acid and/or salts thereof, ethylenediamine tetra acetic acid and/or salts and the like.

The preferred buffering agents useful for purposes of this invention include the weak acids and salts thereof e.g. acetic acid. These acids and salts can be found in the text, incorporated herein by reference, by Williams and Chase entitled Methods in Immunology and Immochemistry, Vol. II, Academic Press, N.Y. (1968).

Basic Blue 54 is characterized as follows:

C.I. No. 11052 Basic Blue 54

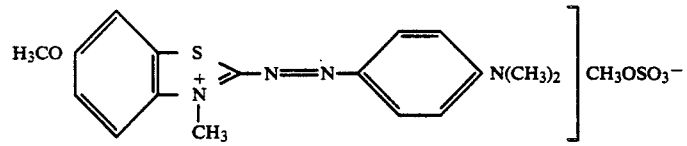

This single substantially pure azo dye is an advance in the field of differentiation and identification of hematopoietic cells, i.e. monocytes as distinguished from other cells obtained from human biopsy specimens.

Specifically, this invention is directed to the use of a sulfur-containing azo dye, identified as C.I. Basic Blue 54(C.I. 11052), to differentially color monocytes in specimens of normal and leukemic human blood. Used in the manner described herein, the dye stains the nuclei and cytoplasm of monocytes a bright red violet color. In contrast, other peripheral blood cells such as neutrophils display little if any cytoplasmic staining, and their nuclei stain brown. Compared with more complex techniques for monocyte identification, Basic Blue 54 provides a distinctive, rapid, easy to use, and colorful stain for monocytes.

More specifically, approximately 14 ml of peripheral venous blood was obtained in evacuated glass tubes containing EDTA (ethylene diamine tetra-acetic acid) from five presumed normal persons. With tubes standing upright at room temperature, erythrocytes sedimented in approximately 2 hours. Using Pasteur pipets, leukocyte rich plasma was removed from the tubes, placed in a separate plastic test tube corresponding to each person, and centrifuged for 5 minutes at 2500 rpm in a Clay Adams desktop centrifuge (Clay Adams, Parsippany, NJ). All but 0.3 ml of the clear supernatant plasma was removed, and the button portion of leukocytes, platelets, and few erythrocytes was resuspended using a Vortex Genie mixer (Scientific Industries, Inc., Bohemia, NY). Films of the leukocyte suspension were made between methanol cleaned coverslips and air dried. Separate coverslips were stained for nonspecific esterase activity using alpha naphthyl butyrate as the substrate, see Yam et al 1971.

As comparisons, peripheral venous blood was obtained at the time of diagnosis and before any treatment from 2 patients with chronic granulocytic leukemia, 2 patients with acute myeloblastic leukemia or Ml by the current FAB (French-American-British) classification (Bennett et al 1985), 3 patients with the M2 variant of acute myeloblastic leukemia, 3 patients with acute promyelocytic leukemia, 2 patients with microgranular promyelocytic leukemia, 2 patients with the M4 variant or acute myelomonocytic leukemia, 2 patients with chronic monocytic leukemia (Bennett et al 1982), and 3 patients with the L2 type of acute lymphoblastic leukemia. On separate panoptically stained specimens from all of these patients as well as on the basis of traditional cytochemical stains including myeloperoxidase, Sudan black B, PAS, nonspecific esterase, specific esterase, and acid phosphatase activities, the cases of acute leukemia were regarded as typical. Patients with the M5, M6 and M7 (Bennett et al 1985b) variants were not available for study.

From the same patients, bone marrow was obtained in heparinized glass syringes by needle aspiration from the posterior iliac crest at the time of diagnosis and prior to any treatment. Films of bone marrow particles were made on methanol cleaned glass coverslips and air dried. For additional comparisons, bone marrow particles were obtained from 2 patients with untreated multiple myeloma and from 3 patients with refractory sideroblastic anemia (Bennett et al 1982) and processed as above.

For all specimens, the staining reaction was performed as follows:

Basic Blue 54 was prepared as a 3% aqueous solution by addition of 10 ml distilled water to 300 mg of the dye powder in the form of Basacryl blue GL (BASF, Charolotte, NC). Prepared in this way, an aqueous solution of Basic Blue 54 was deep red violet in color. On the shelf at room temperature, its staining properties remained unchanged for at least one year. The presence of undissolved dye particles did not seem to interfere with the staining reaction.

The FAA fixative was prepared as a mixture of 90 ml 95% ethyl alcohol, 5 ml acetic acid, and 5 ml 37% formalin. The pH 3.6 acetic acid-sodium acetate buffer was prepared by using acetic acid as a 0.1N solution, prepared by placing 5.7 ml of glacial acetic acid in a volumetric flask, and making up to 1N with distilled water. Sodium acetate was prepared as a 0.1N solution by dissolving 13.6 grams of sodium acetate crystals in distilled water, and making up to 1L with distilled water in a volumetric flask. To make the pH 3.6 buffer, 185 ml of the 0.1N acetic acid solution was added to 15 ml of the 0.1N sodium acetate.

As part of the experiments, other buffers were also tried (Culling 1974). These included acetic acid-sodium acetate buffer with pH ranging from 3.8 to 6.8, 0.2M; Tris (tris hydroxymethylaminomethane) buffer with pH ranging from 7.19 to 9.10, and glycine-NaCl-NaOH buffer with pH ranging from 8.45 to 12.48. However, of all of these buffers, only the acid systems e.g. acetic acid-sodium acetate buffers gave the distinctive color reaction in monocytes described herein.

The specific procedure used is the following:

(a) Fix coverslips in FAA fixative for about 5 minutes, wash by gentle agitation for 10 seconds in a beaker containing distilled water, blot on filter paper, and air dry (b) In a Coplin jar or staining pan, stain the fixed, dried coverslips with the 3% aqueous solution of Basic Blue 54 for about 10 minutes (c) Remove coverslips with a forceps, touch the edge to a piece of gauze to remove excess stain, and agitate for only about 2 seconds in a beaker containing pH 3.6 acetic acid-sodium acetate buffer (d) Place coverslips face down on a piece of filter paper to blot dry, then face up to air dry (e) Mount coverslips on cleaned glass slides with Permount (Fisher Scientific, Pittsburgh PA).

Three different lots of the Basacryl blue GL brand of Basic Blue 54 were used. Also, Basic blue 54 obtained in the form of Astrazon blue GL (Mobay, Pittsburgh) and Sevron blue GLK (Crompton and Knowles, Charlotte, NC) were tried under conditions identical to those described in the case of Basacryl blue GL. In an effort to explain the mechanism(s) of the staining reaction, several different enzymatic digestion methods were used. The first method was used to ascertain whether or not the color visualized in monocytes was due to glycogen. Accordingly, coverslips of normal peripheral blood leukocyte suspensions were fixed in FAA fixative, incubated in diastase (Culling 1974), and subsequently stained with either the PAS stain for glycogen or with Basic Blue 54 as described above. The second method was used to investigate whether the color of monocytes stained with Basic Blue 54 was due largely to RNA. Coverslips of leukocyte suspensions were fixed in FAA fixative, incubated in ribonuclease (Culling 1974), and stained with either methyl green-pyronin or with Basic Blue 54, as described.

To compare the staining properties of other dyes of closely related chemical structures with results obtained with Basic Blue 54, 3% aqueous solutions of Basic Blue 41 (C.I. 11154 (Remacryl blue BRL, Hoechst), Basic Blue 65 (C.I. 11076, Atacryl blue LLA, Atlantic), Basic Blue 66 (C.I. 11075, Atacryl blue LLB, Atlantic) and Basic Blue 67 (C.I. 11185, Atacryl blue LLR, Atlantic) were prepared. Separate coverslips of leukocyte rich plasma and/or bone marrow were fixed and stained in the manner identical to that described in the case of Basic Blue 54, including a terminal rinse in the 3.6 acetic acid-sodium acetate buffer.

For further information regarding the spectral properties of Basic Blue 54, a visible spectrum of an aqueous solution of the dye was obtained in a Beckman Model 35R spectrophotometer. For photomicrography as well as for enhanced visual perception of color differences created by the stain, a didymium filter (Tiffen, Hauppauge, NY) and a #85B orange filter (Tiffen) were placed over the light source of the microscope, after removing any blue filter covering the light source. Stained specimens were photographed using a Zeiss Axioskop and Kodak Ektachrome Tungsten 50 film.

The results were as follows:

In coverslips preparations of normal peripheral blood leukocyte rich plasma, neutrophils displayed brown dense appearing nuclear chromatic, and little if any cytoplasmic staining. Occasionally, a few tiny pink granules appeared. Similarly, lymphocytes showed dark brown nuclear staining, and little if any cytoplasmic staining except in large lymphocytes where the cytoplasm stained pale pink to cream color. In eosinophils, nuclei stained dark brown, and granules were pale green, In basophils, nuclei were dark brown, and granules were orange. Platelets stained pale yellow, and erythrocytes were virtually unstained.

In monocytes stained with Basic Blue 54, nuclei were bright red violet and showed distinctive violaceous strands of chromatin. The cytoplasm of monocytes stained bright red violet as well, and sometimes contained pink and coral colored granules. Using a didymium (color enhancing) filter over the light source of the microscope, the color of monocytes was intensified considerably, making it easy to distinguish monocytes from other peripheral blood leukocytes.

In samples of blood from patients with acute myelomonocytic leukemia and chronic monocytic leukemia, leukemic monocytes displayed intense red violet cytoplasmic and nuclear coloration similar to that found in normal monocytes. In leukemic lymphoblasts and myeloblasts, nuclei stained red to red brown, and cytoplasm stained pale pink or not at all. Similarly, myeloma cells displayed brown nuclear and pink cytoplasmic staining with Basic Blue 54.

In blood and bone marrow samples obtained from patients with chronic granulocytic leukemia, immature granulocytes such as promyelocytes, myelocytes, and metamyelocytes displayed brown nuclei, and cytoplasm that stained yellow to yellow orange depending on the maturity of the cell. In immature cells like promyelocytes, granules stained red and orange. In myelocytes and metamyelocytes, granules stained yellow and orange. Because of differences in color between the red violet nuclei and cytoplasm of monocytes compared with the dark brown nuclei and yellow orange cytoplasmic color of myelocytes and metamyelocytes, it was easy to distinguish monocytes from immature granulocytes on the basis of differences in color.

On coverslips of leukocyte suspension treated with either diastase or ribonuclease and subsequently stained with Basic Blue 54, the color reaction in monocytes showed little if any diminution in hue or chroma. These experiments indicated that the color in monocytes produced by Basic Blue 54 was not due to either glycogen or to RNA.

Although all of the dye lots gave similar results in terms of the color of monocytes, the Basacryl blue GL brand of Basic Blue 54 provided the most intense coloration of monocytes and the most convincing demonstration of differences in color between monocytes and other types of cells. An aqueous solution of Basic Blue 54 had an extinction coefficient with a single peak at 600 nm, see FIG. 1.

Since its identification as a large transitional cell by Ehrlich (Ehrlich and Lazarus 1905) and then as a "monozyten" by Schilling (Schilling 1912), the monocyte has proved to be a cell that is often difficult to identify on the basis of morphology alone. On conventional Wright or Giemsa stained smears viewed under the light microscope, the morphology of monocytes is well known. Yet, it may sometimes be difficult to distinguish monocytes from immature granulocytes, such as myelocytes or metamyelocytes, on the basis of panoptically stained features alone.

As a result, the reaction for nonspecific esterase activity emerged as an enzymatic marker for cells of monocytic or macrophage origin. Nonspecific esterase is a ubiquitous enzyme. When alpha naphthyl acetate or alpha naphthyl butyrate is used as the substrate along with an appropriate dye coupler, activity of the enzyme is intense in monocytes (Yam et al 1971). Under these conditions, nonspecific esterase activity is also found in myelocytes and metamyelocytes, but substantially less intense than in monocytes.

A distinctive feature of monocytic type nonspecific esterase activity is its sensitivity to sodium fluoride when added to the enzyme incubation medium. In normal and leukemic monocytes, nonspecific esterase activity is unusually sensitive to fluoride, and can be obliterated by fluoride (Fischer and Schmalzl 1964). In contrast, nonspecific esterase activity in granulocytic cells in resistant to inhibition by fluoride, and the enzyme reaction product shows little if any diminution in color or intensity in these cells. As it is formulated presently, the stain for nonspecific esterase activity involves a complex reaction mixture made of several unstable reactants that must be prepared immediately before use (Yam et al 1971).

More specifically, this invention involves staining fixed monocytes with an aqueous solution of Basic Blue 54 and then treating the stained cells to a terminal acid rinse e.g. a pH 3.6 acetic acid-sodium acetate buffer. Under these conditions, and enhanced with appropriate color filters, monocytes display bright red violet coloration of both nucleus and cytoplasm. In other types of normal peripheral blood leukocytes and in leukemic myeloplasts and lymphoblasts, coloration of the type found in monocytes was not observed.

Further, Basic Blue 54 yielded differences in color when comparing monocytes with immature granulocytes such as myelocytes and metamyelocytes. Using Basic Blue 54, it was easy to distinguish the bright red violet coloration of monocyte nucleus and cytoplasm from the dark brown nuclear color and yellow orange cytoplasmic color of myelocytes and metamyelocytes. At the present time, the substance(s) responsible for the distinctive red violet coloration of both nucleus and cytoplasm of monocytes is unknown.

Following the 10 minute staining period, a brief treatment of the stained cells with an acetic acid-sodium acetate buffer at an acid pH (e.g. pH ranging from about 2.0 to 6.0) was essential for optimal development of the red violet color in monocytes. Moreover, in the same preparations, other cells including mature and immature granulocytes and lymphocytes also stained intensely, making it difficult to distinguish monocytes from other cells that may superficially resemble them. As the pH of the acetic acid-sodium acetate buffer was lowered progressively, the cytoplasmic coloration of cells other than monocytes became progressively fainter and in some instances disappeared entirely. In contrast, as the pH of the buffer declined to the optimal level of 3.6, the red violet color of the nucleus and cytoplasm of the monocyte remained intact and undiminished. The distinctive red violet nuclear and cytoplasmic color of monocyte stained with Basic Blue 54 seemed to resist decolorization when exposed to an acid buffer.

Provided that the usual precautions are taken according to the manufacturer's MSDS information, Basic Blue 54 has not been reported as having unusual toxicity. In contrast to other sulfur containing azo dyes of related chemical structure only Basic Blue 54 gave selective coloration of monocytes under the specific conditions described herein.

Compared with the traditional stain for nonspecific esterase activity, the Basic Blue 54 stain for monocytes is easier to perform, involves fewer reagents, does not require a complex unstable incubation mixture prepared before use, and does not require an enzyme inhibitor. Further studies on additional cases of monocytic leukemia will help to establish whether or not Basic Blue 54 is as specific for monocytes as the conventional fluoride sensitive nonspecific esterase stain. Likewise, additional studies on macrophages obtained from bronchial lavage specimens will help to determine whether or not Basic Blue 54 is a colorant for these macrophages and can be used to distinguish them from other cells. As a new colorant for monocytes when used in the manner described, Basic Blue 54 is a valuable addition to the hematological cytochemistry laboratory.

The following examples illustrate the combination of Basic Blue 54 with cells and the use of said dye in accordance with this invention.

EXAMPLE 1

A 45 year old white male was admitted to the hospital because of weakness, anemia, and thrombocytopenia. He also complained of nosebleeds over the month prior to admission. On physical examination, he was pale with blood pressure 135/82 and pulse 90/minute and regular. Pertinent findings on physical examination was an enlarged spleen, palpable 6 cm below the left costal margin. Laboratory revealed hemoglobin 6.4 grams %, hematocrit 18.2%, white blood cell count 185,000/mm3, and a platelet count 22,000/mm3. Using a conventional Wright's stain, a differential cell count on the patient's peripheral blood smear disclosed 12% neutrophils, and 88% monocytes, many of which appeared immature. Using Basic Blue 54 and an acid rinse on a duplicate slide, monocytes were easily detectable on the basis of their distinctive red violet color and numbered approximately 90% of the total cells counted. As confirmed on a bone marrow examination, the diagnosis was acute myelomonocytic leukemia.

EXAMPLE 2

A 76 year old oriental female was seen in the doctor's office because of fatigue and petechiae over a period of 4 months prior to admission. She also complained of frequent infections, such as sinusitis and cellulitis. On physical examination, blood pressure was 100/64, pulse 100 and regular and she was afebrile. On physical examination, the spleen was palpable 4 cm below the left costal margin, and the liver was palpable 6 cm below the right costal margin. Laboratory values included hemoglobin 8.3 grams %, hematocrit 25.4%, white blood cell count 26,480/mm3 and platelet count was 16,000/mm3. On a Wright's stained smear of the peripheral blood, there were 10% neutrophils, 2% lymphocytes, 3% eosinophils, and 85% monocytes. Using Basic Blue 54 and an acid rinse on a duplicate blood smear, a similar differential cell count was obtained. A bone marrow aspiration showed approximately 25% monocytes when stained with either Wright's stain or Basic Blue 54. The diagnosis was chronic monocytic leukemia (myelodysplastic syndrome).

EXAMPLE 3

A 38 year old black male who had received combination chemotherapy for acute myeloblastic leukemia three weeks earlier came to the doctor's office complaining of weakness and fatigue. On physical examination, blood pressure was 118/62, pulse 100 and regular, and he was afebrile. Aside from alopecia due to chemotherapy, the physical examination was unremarkable. Laboratory values included hemoglobin 11.3 grams %, hematocrit 33.2%, white blood cell count 2,300/mm3, and platelet count 122,000/mm3. On a peripheral blood smear stained with Wright's stain, the differential showed 33% neutrophils, 7% bands, 30% monocytes, 20% lymphocytes, 5% eosinophils, and 5% basophils. On a duplicate smear stained with Basic Blue 54 and an acid rinse, a similar differential cell count was obtained. A bone marrow aspirate stained with either Wright's stain or Basic Blue 54 demonstrated approximately 10% monocytes. The diagnosis was reactive monocytosis in a regenerating bone marrow following combination chemotherapy for acute leukemia.

Leukemia is a disease characterized by an increase in the number of leukocytes and their precursors in the blood. Other symptoms are enlargement and proliferation of the lymphoid tissue of the spleen and lymphatic glands, and marked increase in immature cells in the bone marrow. Leukemia is classified clinically on the basis of (1) duration and character of the disease—acute or chronic; (2) type of cell involved myeloid (myelogenous), lymphoid (lymphogenous) or monocytic; (3) increase or nonincrease in the number of abnormal cells in the blood-leukemic.

As a single agent stain of substantial purity, Basic Blue 54 has certain advantages when compared to the traditional stains. These include the lack of unstable reaction products, a broad range of hue and chroma, brilliance of coloration, and the ability to stain aged fixed specimens. In contrast to the degradability of Romanowsky type stains in methanol, a methannolic solution of Basic Blue 54 on the shelf at room temperature for one year showed no noticeable diminution or alteration of staining properties.

The references cited herein are as follows:
1. Bennett, J.M., Catovsky, D., Daniel, M.T. et al. 1982 Proposals for the classification of the myelodysplastic syndromes. Brit. J. Haematol. 51:189–199.
2. Bennett, J.M., Catovsky, D., Daniel, M.T. et al. 1985a. Proposed revised criteria for the classification of acute myeloid leukemia. A report of the French-American-British Cooperative Group. Ann. Intern. Med. 103:620–625.
3. Bennett, J.M. Catovsky, D. Daniel, M.T. et al. 1985b. Criteria for the diagnosis of acute leukemia of megakaryocyte lineage (M7). A report of the French-American-British Cooperative Group. Ann. Intern. Med. 103:460–462.
4. Culling, D.F.A. 1974. Handbook of Histopathological and Histochemical Techniques. Third Edition. London, Butterworths, pp. 167–177.
5. Ehrlich, P. and Lazarus, A. 1905. Anemia. Histology of the blood, normal and pathologic. In Diseases of the Blood. A. Stengel, Ed. Saunders, Philadelphia. pp 17–150.

6. Fischer, R. and Schmalzl, F. 1964. Uber die Hemmbarkeit der Esteraseaktivitat in Blutmonocyten durch Natrium fluorid. Klin. Wochenschr. 42:751.

7. Kass, L. 1988. Basic blue 41: A new panoptic stain for blood and bone marrow cells. J. Histotechnol. 11:10–14

8. Schilling, V. 1912. Das Blutbild und seine klinische Verwertung (mit Einschluss der Tropenkrankheiten); kurzgefasste technische, theoretische und praktische Anleitung zur mikroskopischen Blutuntersuchung. Jena, G. Fischer.

9. Yam, L.T., Li, C.Y., and Crosby, W.H. 1971. Cytochemical identification of monocytes and granulocytes. Am.J. Clin. Pathol. 55: 283–290.

While this invention has been described by a number of specific examples, it is obvious that there are other variations and modifications which can be made without departing from the scope of the invention as particularly set forth in the appended claims.

The invention claimed is:

1. A method for staining a plurality of cells for differentiating, identifying and enumerating monocytes which comprises obtaining a plurality of cells of hematopoietic origin selected from the group consisting of blood cells, bone marrow cells and lymph node cells, fixing said cells in a fixative, staining said fixed cells with a staining amount of a water soluble azo dye, identified as Basic Blue 54 (C.I. 11052) to obtain a plurality of stained cells and subsequently treating the stained cells with an acid buffer; said stained cells having color characteristics which enable the differentiation, identification and enumeration of the monocytes from the other cells.

2. The method of claim 1 wherein the stained cells are stained such that they have color characteristics which enable the differentiation, identification and enumeration of monocytes by use of an absorbance light source.

3. The method of claim 1 wherein the stained cells are stained such that they have color characteristics which enable the differentiation, identification and enumeration of monocytes by use of an instrument.

4. The method of claim 1, wherein the cells of hematopoietic origin are blood cells.

5. The method of claim 1 wherein the cells of hematopoietic origin are lymph node cells.

6. The method of claim 1 wherein the cells of hematopoietic origin are bone marrow cells comprising erythrocytes, platelets, neutrophils, lymphocytes, monocytes, eosinophils, basophils, megakaryocytes, plasma cells, macrophage, proerythroblasts, normoblasts, promyelocytes, neutrophilic myelocytes, neutrophilic metamyelocytes, bands, and mast cells, 7. The method of claim 1 wherein the fixative comprises a lower molecular weight alcohol.

8. The method of claim 1 wherein the fixative comprises formaldehyde.

9. The method of claim 7 wherein the alcohol fixative contains up to about 2.0% by weight of the azo dye in solution.

10. The method of claim 9 wherein the fixative comprises absolute methyl alcohol and staining amounts of the azo dye ranging up to about 1% by weight.

11. The method of claim 9 wherein the cells of hematopoietic origin are fixed in an aqueous solution of absolute methyl alcohol and then stained with staining amounts of the water soluble azo dye.

12. The method of claim 9 wherein the cells of hematopoietic origin are human blood cells.

13. The method of claim 9 wherein the cells of hematopoietic origin are bone marrow cells comprising erythrocytes, platelets, neutrophils, lymphocytes, monocytes, eosinophils, basophils, megakaryocytes, plasma cells, macrophage and proerythroblasts.

14. The method of claim 9 wherein the cells of hematopoietic origin are blood cells comprising monocytes, platelets, eosinophils, basophils, B-lymphocytes, T-suppressor cells, T-helper cells, and Natural Killer cells.

15. The method of claim 12 wherein the human blood cells comprise cells surrounded by parasites.

16. The method of claim 12 wherein the human blood cells comprise malignant cells.

17. The method of claim 9 wherein the cells of hematopoietic origin comprise malignant cells.

18. The method of claim 12 wherein the stained cells are stained such that they have color characteristics which enable the differentiation, identification and enumeration of monocytes by use of an image analyzer.

19. The method of claim 12 wherein the stained cells are stained such that they have color characteristics which enable the differentiation, identification and enumeration of monocytes by use of an absorbance light source.

20. The method of claim 12 wherein the stained cells are stained such that they have color characteristics which enable the differentiation, identification and enumeration of monocytes by use of a microscope.

21. The method of claim 1 wherein the buffer treatment is at a pH ranging from about 2.0 to 6.0.

22. The method of claim 21 wherein the buffer is an acid rinse comprising acetic acid.

23. A plurality of cells of hematopoietic origin selected from the group consisting of blood cells, bone marrow cells, and lymph node cells fixed and stained with an azo dye, identified as Basic Blue 54 ( C.I. 11052) and subsequently treated with an acid buffer; said plurality of cells having color characteristics which enable the differentiation, identification and enumeration of monocytes among said plurality of cells.

24. The plurality of cells of hematopoietic orifin of claim 23 wherein said plurality of cells are blood cells comprising T-helper cells, T-suppressor cells, B-cells, Natural Killer cells, neutrophils, basophils, eosinophils, monocytes, and platelets.

25. The plurality of cells of hematopoietic origin of claim 23 wherein said plurality of cells comprise stained monocytes having a red-violet color.

26. The plurality of cells of hematepoietic origin of claim 25 wherein said stained monocytes comprise malignant cells.

* * * * *